United States Patent [19]

Irick, Jr. et al.

[11] Patent Number: 5,254,596
[45] Date of Patent: Oct. 19, 1993

[54] PROCESS FOR THE MANUFACTURE OF METHANOL AND DIMETHYL ETHER

[75] Inventors: Gether Irick, Jr., Gray; Patricia N. Mercer; Keneth E. Simmons, both of Kingsport, all of Tenn.

[73] Assignee: Eastman Kodak Company, Rochester, N.Y.

[21] Appl. No.: 945,048

[22] Filed: Sep. 15, 1992

[51] Int. Cl.$^5$ .............................................. C07C 27/06
[52] U.S. Cl. ...................................................... 518/728
[58] Field of Search ......................................... 518/728

[56] References Cited

FOREIGN PATENT DOCUMENTS 1159035 7/1969 United Kingdom .

OTHER PUBLICATIONS

Villa et al, Applied Catalysis, 35 (1987) pp. 47-58.

*Primary Examiner*—Howard T. Mars
*Attorney, Agent, or Firm*—J. Frederick Thomsen; William P. Heath, Jr.

[57] ABSTRACT

Disclosed are chemically-mixed, titanium-zinc oxide catalysts and the use of the catalysts in the manufacture of methanol and dimethyl ether wherein synthesis gas is contacted at elevated temperatures and pressures with the catalyst.

5 Claims, No Drawings

PROCESS FOR THE MANUFACTURE OF METHANOL AND DIMETHYL ETHER

This invention pertains to a process for the manufacture of methanol and dimethyl ether wherein synthesis gas is contacted at elevated temperatures and pressures with a catalyst comprising chemically mixed, titanium-zinc oxide. This invention also pertains to the chemically mixed, titanium-zinc oxide catalysts employed in the process described.

Methanol has been an important solvent and chemical intermediate for many years and is produced in greater than billion pound quantities in several different countries. Dimethyl ether is useful as the feedstock in carbonylation processes for the manufacture of acetic anhydride. The catalyst of choice for methanol production from synthesis gas (mixture of hydrogen, carbon monoxide and carbon dioxide) for many years has been a zinc-chromium mixed oxide. However, this catalyst now has been largely replaced by catalysts based on copper-zinc. The former contains the toxic metal chromium and the latter is highly sensitive to poisoning by impurities in the synthesis gas reactant and to sintering and deactivation by overheating. Supported palladium catalysts have been shown to be highly selective in the conversion of synthesis gas to methanol, but their high cost has precluded their commercialization to date.

The conversion of synthesis gas to methanol using zinc chromium oxide catalysts has been known since the early 1920's [E. Fiedler, G. Grossmann, B. Kersebohm, G. Weiss, and Claus Witte, Ullmann's Encyclopedia of Industrial Chemistry, 5th Edition, Volume A16, VCH, Weinheim FRG, 1990, pp. 465-484 and H. F. Woodward, Jr., Kirk-Othmer Encyclopedia of Chemical Technology, 2nd Edition, Volume 13, John Wiley, NY, 1967, pp. 370-398]. The zinc chromium oxide catalysts are very resistant to impurities in the synthesis gas feed, but the toxicity of the chromium presents major waste disposal problems.

The other catalyst which has seen widespread commercial acceptance in the synthesis of methanol is based on copper zinc oxides. Such catalysts have very favorable operating conditions but are very sensitive to impurities in the synthesis gas feed. A recent review of methanol synthesis over the copper-zinc catalysts was provided by J. C. J. Bart and R. P. A. Sneeden, Catalysis Today 2(1), 1-124 (1987). U.S. Pat. No. 4,929,777 describes the use of chemically-mixed, copper titanium oxides as hydrogenation catalysts, e.g. in the hydrogenolysis of esters to alcohols.

According to Advances in Catalysis V31, pp 243-313; D. D. Eley, Herman Pines and P. B. Weisz editors, AP, NY (1982), pure zinc oxide is a very poor methanol catalyst at 250° C. and 75 atmospheres pressure and exhibits relatively high activity only at pressures exceeding 200 atmospheres and at temperatures above 350° C. Zinc-titania mixed oxides containing about 7 or 57% zinc oxide were prepared by Kozo Tanabe et al [Bull. Chem. Soc. Japan, Vol. 45, pp 47-51 (1972)] and found to be fairly strong acids. They were not investigated for use in catalyzing the hydrogenation of synthesis gas to methanol.

P. Villa et al have reported in Applied Catalysis V35, pp 47-58 (1987) the preparation of zinc-titanias having Zn:Ti ratios of 1.0, 1.5 and 2.0 and the addition of potassium (0, 3, and 5% as the oxide after final catalyst treatments) to the zinc titanias. When the potassium modified, zinc titania catalysts were evaluated in the hydrogenation of carbon monoxide, the catalysts produced more methane than methanol and, in many cases, even produced more $C_2$ hydrocarbons than methanol. For example, the catalyst which contained the lowest concentration of zinc (50%) produced significantly more methane and higher hydrocarbons than methanol.

We have discovered that catalysts comprising chemically-mixed, titanium-zinc oxide wherein the zinc constitutes less than 50 weight percent of the titanium-zinc oxide exhibit good to excellent activity and selectivity in converting synthesis gas to methanol and dimethyl ether. The present invention therefore provides a process for the preparation of methanol, dimethyl ether or a mixture thereof which comprises contacting synthesis gas with a catalyst comprising chemically-mixed, titanium-zinc oxide wherein the Zn:Ti atomic ratio is in the range of 0.025:1 to 0.58:1.

The catalysts employed in our novel process do not require the presence of either chromium, copper, nor palladium. To the contrary, the presence of these metals often is detrimental to the high methanol/dimethyl ether selectivity demonstrated by the catalysts of this invention. Therefore, the catalysts employed in our invention preferably are essentially free of chromium, copper, and palladium, e.g., such metals constitute less than about 0.1 weight percent of the total weight of the catalyst. However, other metals such as manganese, iron, sodium, potassium, lanthanum, magnesium and related metals having basic oxides may be present to increase catalyst lifetime and/or improve performance. Such metals are not essential to the performance of the catalyst in converting synthesis gas to methanol and its dehydration product dimethyl ether while keeping methane and other hydrocarbon makes well below 50% and in many case less than 10%.

The essential ingredients of the catalyst are chemically mixed, zinc titanium oxides which contain —Ti—O—Zn— bonds. The Zn:Ti atomic ratio preferably is in the range of about 0.025:1 to 0.58 which corresponds to a zinc content of about 2 to 30 weight percent. The essential ingredient, i.e., the chemically mixed, zinc titanium oxides, of the novel catalyst compositions may be further defined by the formula $$Zn_xTi_yO_z$$

wherein x, y, and z represent atomic ratios and x is about 0.025 to 0.58, y is 1.0 and z is about 2.03 to 2.58. The particularly preferred catalyst compositions are those wherein x is about 0.07 to 0.28, y is 1.0 and z is about 2.07 to 2.28.

In addition to the mixed Zinc titanium oxides, the catalyst compositions may contain or be deposited on or in other materials. For example, we expect that the production of methanol (rather than dimethyl ether) may be enhanced by the inclusion of minor amounts, e.g., up to about 10 weight percent, of other metals such as Li, Na, K, Rb, Cs, Mg, Ca, Sr, Ba, La, Ce or possibly other elements which form basic oxides. The maximum benefit of these basic modifiers should be accomplished when they are present in a concentration of about 0.2 to 3.0 weight percent, based on the weights of the basic metals and the total catalyst. It also may be desirable to add "structural promoters" to the catalysts to increase surface area or to change the acidity/basicity to optimize performance of the catalyst in a specific process. Such structural promoters as the oxides of silicon, aluminum, germanium, boron, tin, etc. can be combined with the catalysts during their preparation. Alternatively, the catalysts may be deposited on such oxides, for example, by preparing the catalysts in the presence of such an oxide of a particular shape or particle size.

Our novel catalyst compositions can be used in the form of powders, cylinders, spheres, honeycombs, etc., the physical form being dictated by the type of reactor chosen for and by economic and engineering considerations associated with a particular hydrogenation process. Frequently, it will be desirable to use a binder to assist in the formation and maintenance of the catalyst compositions in a particular shape. For example, alumina, clays and zirconia are commonly used binders in the manufacture of commercial catalyst pellets or cylinders.

The catalyst compositions of this invention may be prepared by a variety of methods. Generally, suitable procedures are described in Volumes 1 and 3 of Studies in Surface Science and Catalysis, Elsevier Scientific Publishing Company. The source of the titanium component of our catalysts may be titanium tetrachloride, tetraisopropyl titanate, titania sol, titanium bromide, titanium butoxide, titanium methoxide, titanium butoxybis-(2,4-pentanedionate), titanium oxides, etc. Compounds which may be used as the source of the zinc component include zinc nitrate, zinc halides such as zinc chloride and zinc bromide, and zinc alkanoates such as zinc acetate, zinc propionate and zinc octanoate.

The titanium and zinc compounds may be physically mixed, heated in air at temperatures above 500° C., ground and then reheated. Where appropriate, hydrous titania can be precipitated and treated with a soluble zinc salt such as a chloride, bromide, acetate or nitrate followed by drying and calcining in air at 550° C. Another procedure comprises coating a soluble zinc compound onto the surface of an amorphous form of titanium oxide (hydrous oxide), followed by calcining in air. The exact method of preparation is not critical so long as the formation of —Ti—O—Zn— is achieved. This bonding distinguishes the essential or active ingredient of our catalysts from those in which copper is merely deposited on the surface of a support and exists primarily as a —Zn—O—Zn— species. Other elements or compounds, such as those specified hereinabove, may be added to the titanium and zinc sources during preparation of the catalyst.

The synthesis gas which functions as the reactant in our novel process typically comprises about 5 to 33 volume percent carbon monoxide and about 67 to 95 volume percent hydrogen. The synthesis gas optionally may contain other compounds such as up to about 20 volume percent carbon dioxide. The synthesis gas preferably comprises about 8 to 20 volume percent carbon monoxide, about 72 to 92 hydrogen and 0 to 20 volume percent carbon dioxide. The advantages of including a small amount of carbon dioxide in synthesis gas used in the manufacture of methanol are well documented. See, for example, G. J. Millar et al, Catalysis Letters, 14, 289–295 (1992) and K. C. Waugh, Catalysis Today, 15, 51–75 (1992).

The process may be carried out at temperatures in the range of about 200° to 350° C. and pressures of about 700 to 5500 psig. A minimum operating temperature of 230° C. is preferred to provide attractive production rates. Preferred operating conditions are temperatures and pressures of about 230° to 275° C. and 1000 and 3000 psig.

The catalyst compositions and process provided by our invention are further illustrated by the following examples.

EXAMPLE 1

Tetraisopropyl titanate (344.2 g) was added to 1000 mL of water with stirring and the resulting white slurry stirred for 1 hour. The solid was filtered, washed with water, and re-slurried in water. The pH was adjusted to 10 with ammonium hydroxide, the slurry stirred at 60° C. for 3 hours, cooled to 25° C. and filtered. The white solid was added to a solution of 49.8 g zinc nitrate in 900 mL water and the mixture was heated at 60° C. for 3 hours, cooled, filtered, washed with water and dried at 100° C. The solid was then calcined in air at 200° C., 350° C., and finally 550° C. The white solid catalyst thus obtained contained 12 weight percent zinc and had the formula $Zn_{0.17}TiO_{2.17}$.

EXAMPLE 2

Tetraisopropyl titanate (172.1 g) was added in 15 minutes to 500 mL water with stirring, and the mixture stirred at room temperature for 1 hour. The white solid was slurried in water, refiltered and slurried in water. The pH was adjusted to 10 with ammonium hydroxide and the slurry was stirred 3 hr at 60° C., cooled and filtered. The solid obtained was added to a solution of 24.9 g zinc nitrate hexahydrate in 450 mL water and the mixture was heated at 60° C. for 3 hours. The mixture then was cooled to room temperature, filtered, washed with distilled water, and dried at 100° C. The solid was then calcined in air at 200° C., 350° C., and finally at 450° C. for 3 hours. The white solid catalyst obtained contained 10 weight percent zinc, had a BET surface area 115 square meters per g ($m^2/g$) and had the formula $Zn_{0.14}TiO_{2.14}$.

EXAMPLE 3

The procedure of Example 2 was repeated using 284.22 g of tetraisopropyl titanate and 20.6 g of zinc nitrate to produce a catalyst containing 8 weight percent zinc and having the formula $Zn_{0.11}TiO_{2.11}$.

EXAMPLE 4

The procedure of Example 2 was repeated using 284.22 g of tetraisopropyl titanate and 8.47 g of zinc nitrate to produce a catalyst containing 3.5 weight percent zinc and having the formula $Zn_{0.045}TiO_{2.045}$.

EXAMPLE 5

The procedure of Example 2 was repeated using 284.22 g of tetraisopropyl titanate and 4.26 g of zinc nitrate to produce a catalyst containing 1.8 weight percent zinc and having the formula $Zn_{0.22}TiO_{2.022}$.

EXAMPLE 6

Tetraisopropyl titanate (172.1 g) was added to 500 mL water and the resulting slurry was stirred for 1 hr at 25° C., filtered, washed with water, refiltered and then slurried in about 300 mL water. Ammonium hydroxide was then added to pH 10 and the mixture stirred 3 hrs at 60° C., filtered and then added to a solution of 12.45 g zinc nitrate and 16.91 g ferric nitrate hydrate in 450 mL water. The slurry was stirred 3 hrs at 60° C., cooled to 25° C., filtered, washed with about 100 ml water and filtered. The solid was dried at 100° C. and then was calcined in air at 200° C., then at 350° C., and finally at 450° C. for 3 hours. The catalyst thus prepared contained 5 weight percent zinc and 5 weight percent iron and had the formula $Zn_{0.068}Fe_{0.086}TiO_{2.2}$.

EXAMPLE 7-10

Tetraisopropyl titanate (172.1 g) was added to 500 mL water and stirring was continued for 1 hour. The solid was filtered off, washed with water and refiltered. The wet solid was slurried in about 300 mL water, ammonium hydroxide was added to pH 10, and the slurry was stirred at 60° C. for 3 hours, cooled to 25° C. and filtered. The white solid then was added to a solution of 24.9 g zinc nitrate in 450 mL water and the slurry was stirred at 60° C. for 3 hours. The mixture was cooled to 25° C., filtered, washed with 100 mL water, dried at 100° C. and then calcined in air at 200° C., 350° C., and finally 450° C. for 3 hours.

A 5 g aliquot of the zinc-titanium oxide prepared as described in the preceding paragraph was slurried in water at 75°-80° C. and a pH of 10 for 3 hours, filtered, reslurried in water and then refiltered. The solid obtained then was slurried in 200 mL water and a solution of ferric nitrate nonahydrate in 10 mL water was added to provide a catalyst containing 0.1 weight percent Fe. The resulting slurry was stirred 3 hours at 60° C., cooled to 25° C., filtered and washed with 150 mL water. The solids were then dried at 100° C. and calcined in air for 3 hours at 250° C. to provide a catalyst (Example 7) containing 10 weight percent zinc and 0.5 weight percent iron [Fe].

Additional 5 g aliquots of the zinc-titanium oxide material were treated with solutions of ferric nitrate nonahydrate in 10 mL water as described above to provide catalysts containing 10 weight percent zinc and 1.0 weight percent iron (Example 8), 10 weight percent zinc and 2.0 weight percent iron (Example 9), and 10 weight percent zinc and 3.0 weight percent iron (Example 10).

EXAMPLE 11-16

Procedures similar to those described in Examples 7-10 were employed to prepare chemically-mixed, zinc-titanium oxide catalysts containing:

Example 11: 10 weight percent zinc and 0.5 weight percent ruthenium.

Example 12: 10 weight percent zinc and 2 weight percent manganese.

Example 13: 10 weight percent zinc and 5 weight percent additional zinc which was applied to a 10% zinc-modified titania which has been calcined at 450° C.

Example 14: 10 weight percent zinc and 2 weight percent copper.

Example 15: 10 weight percent zinc and 5 weight percent copper.

Example 16: 10 weight percent zinc and 1 weight percent potassium

EXAMPLES 17-25

The catalysts described in certain of the preceding examples were evaluated in the conversion of synthesis gas to methanol and dimethyl ether. The apparatus used consisted of a 3/16-inch interior diameter, stainless steel, tubular reactor in which was placed 1 mL (approximately 1 g) of catalyst held in place with quartz wool plugs above and below the catalyst bed. The reactor was enclosed in an electrically heated furnace to provide temperature control. Synthesis gas consisting of 75 volume percent hydrogen and 25 volume percent carbon monoxide was fed, using Brooks flow controllers, to the top of the reactor. The pressure of the off-gas removed from the bottom of the reactor was reduced to atmospheric pressure, cooled in a glycol condenser system and the resulting liquid and gas phases were analyzed by gas chromatography.

Each catalyst sample was pretreated with either hydrogen or synthesis gas below 250° C. and then was brought to 300° C. with preheated synthesis gas. The gas hourly space velocity (GHSV) for the synthesis gas was 12,000. GHSV is the mL of synthesis gas fed per hour divided by the mL of catalyst bed. The pressure within the reactor was 1200 psi.

The results obtained in Examples 17-25 are given in Table I. The numerical designation for the catalyst (Cat) used in each example refers to the example which describes its preparation. The Methanol Formation Rate values are grams methanol produced per gram of catalyst per hour. Carbon Selectivities means the atomic carbon of the carbon monoxide converted which is present in the products, i.e., methanol, dimethyl ether and methane.

TABLE I

| | | Methanol Formation | Carbon Selectivities | | |
|---|---|---|---|---|---|
| Example | Cat | Rate | Methanol | Dimethyl Ether | Methane |
| 17 | 2 | 0.27 | 81 | 17 | 2 |
| 18 | 6 | 0.12 | 63 | 32 | 5 |
| 19 | 8 | 0.2 | 76 | 21 | 3 |
| 20 | 11 | 0.08 | 39 | 0 | 28 |
| 21 | 12 | 0.43 | 74 | 24 | 2 |
| 22 | 13 | 0.01 | 91 | 6 | 2 |
| 23 | 14 | 0.39 | 70 | 19 | 11 |
| 24 | 15 | 0.15 | 53 | 29 | 16 |
| 25 | 16 | 0.1 | 54 | 43 | 1 |

EXAMPLES 26-30

Using the general procedure described in Examples 17-25, the effect of varying reaction temperature using the catalyst of Example 2 was determined. In Examples 26 and 27 the synthesis gas used consisted of 67 volume percent hydrogen and 33 volume percent carbon monoxide and the synthesis gas used in Examples 28-30 consisted of 75 volume percent hydrogen and 25 volume percent carbon monoxide. A gas pressure of 900 to 1200 psi was used in all of the examples. The GHSV of the synthesis gas was 12,000.

The results obtained are shown in Table II wherein Temp is the reaction temperature in °C. and Methanol Formation Rate and Carbon Selectivities have the meanings given hereinabove. Examples 29 and 30 gave 4-6% ethane and other hydrocarbons in addition to the compounds reported in Table II.

TABLE II

| | | Methanol Formation | Carbon Selectivities | | |
|---|---|---|---|---|---|
| Example | Temp | Rate | Methanol | Dimethyl Ether | Methane |
| 26 | 250 | 0.05 | 94 | 5 | 0.4 |
| 27 | 275 | 0.08 | 83 | 15 | 0.8 |
| 28 | 300 | 0.10 | 56 | 39 | 3 |
| 29 | 325 | 0.80 | 29 | 60 | 5 |
| 30 | 350 | 0.33 | 15 | 67 | 10 |

As can be seen from the data of Table II, high selectivity to methanol and dimethyl ether was observed over the 250°-350° C. operating range, but the least methane by-product was observed below 325° C.

The invention has been described in detail with particular reference to preferred embodiments thereof, but it will be understood that variations and modifications will be effected within the spirit and scope of the invention.

We claim:

1. Process for the preparation of methanol, dimethyl ether or a mixture thereof which comprises contacting synthesis gas with a catalyst comprising chemically-mixed, titanium-zinc oxide wherein the Zn:Ti atomic ratio is in the range of 0.025:1 to 0.58:1 wherein the process is carried out at a temperature of about 200° to 350° and a pressure of about 700 to 5500 psig.

2. Process according to claim 1 wherein the catalyst further contains about 0.2 to 2.0 weight percent of Li, Na, K, Rb, Cs, Mg, Ca, Sr, Ba, La or Ce.

3. Process according to claim 1 wherein the synthesis gas comprises about 5 to 33 volume percent carbon monoxide and about 67 to 95 volume percent hydrogen.

4. Process for the preparation of methanol, dimethyl ether or a mixture thereof which comprises contacting synthesis gas comprising about 5 to 33 volume percent carbon monoxide and about 67 to 95 volume percent hydrogen with a catalyst composition essentially free of chromium, copper, and palladium comprising chemically-mixed, titanium zinc oxide having the formula $$Zn_xTi_yO_z$$

wherein x, y, and z represent atomic ratios and x is about 0.025 to 0.58, y is 1.0 and z is about 2.03 to 2.58 at a temperature of about 200° to 350° C. and a pressure of about 700 to 5500 psig.

5. Process according to claim 4 for the preparation of methanol, dimethyl ether or a mixture thereof which comprises contacting synthesis gas comprising about 8 to 20 volume percent carbon monoxide, about 72 to 92 volume percent hydrogen and up to 20 volume percent carbon dioxide with a catalyst composition essentially free of chromium, copper, and palladium comprising chemically-mixed, titanium-zinc oxide having the formula $$Zn_xTi_yO_z$$

wherein x, y, and z represent atomic ratios and x is about 0.07 to 0.28, y is 1.0 and z is about 2.07 to 2.28 at a temperature of about 230° to 275° C. and a pressure of about 1000 to 3000 psig.

* * * * *